United States Patent
Chen et al.

(10) Patent No.: US 10,736,887 B2
(45) Date of Patent: Aug. 11, 2020

(54) QUINOLINE DERIVATIVE FOR TREATING GASTRIC CANCER

(71) Applicant: CHIA TAI TIANQING PHARMACEUTICAL GROUP CO., LTD., Jiangsu (CN)

(72) Inventors: Jie Chen, Jiangsu (CN); Xi Han, Jiangsu (CN); Hai Jiang, Jiangsu (CN); Xunqiang Wang, Jiangsu (CN)

( * ) Notice: Subject to any disclaimer, the term of this patent is extended or adjusted under 35 U.S.C. 154(b) by 0 days.

(21) Appl. No.: 16/092,745

(22) PCT Filed: Apr. 14, 2017

(86) PCT No.: PCT/CN2017/080563
§ 371 (c)(1),
(2) Date: Oct. 10, 2018

(87) PCT Pub. No.: WO2017/177962
PCT Pub. Date: Oct. 19, 2017

(65) Prior Publication Data
US 2019/0125739 A1    May 2, 2019

(30) Foreign Application Priority Data

Apr. 15, 2016    (CN) .......................... 2016 1 0238157

(51) Int. Cl.
| | | |
|---|---|---|
| A61K 31/4709 | (2006.01) | |
| A61P 35/04 | (2006.01) | |
| A61K 9/00 | (2006.01) | |
| A61K 9/20 | (2006.01) | |
| A61K 9/48 | (2006.01) | |
| A61K 45/06 | (2006.01) | |

(52) U.S. Cl.
CPC ........ *A61K 31/4709* (2013.01); *A61K 9/0053* (2013.01); *A61K 9/20* (2013.01); *A61K 9/48* (2013.01); *A61P 35/04* (2018.01); *A61K 45/06* (2013.01)

(58) Field of Classification Search
CPC .... A61K 31/4709; A61K 9/0053; A61K 9/20; A61K 9/48; A61K 45/06; A61P 35/04
See application file for complete search history.

(56) References Cited

U.S. PATENT DOCUMENTS

| | | | |
|---|---|---|---|
| 7,667,039 B2 | 2/2010 | Garcia-Echeverria et al. | |
| 8,148,532 B2 | 4/2012 | Chen | |
| 9,550,781 B2 | 1/2017 | Xiao | |
| 9,725,439 B2 | 8/2017 | Xiao et al. | |
| 9,751,859 B2 | 9/2017 | Chen | |
| 9,968,597 B2 | 5/2018 | Zhang et al. | |
| 10,100,034 B2 | 10/2018 | Chen | |
| 10,112,945 B2 | 10/2018 | Chen et al. | |
| 10,183,017 B2 | 1/2019 | Zhang et al. | |
| 10,251,876 B2 | 4/2019 | Wang et al. | |
| 10,307,412 B2 | 6/2019 | Wang et al. | |
| 2010/0105696 A1 | 4/2010 | Garcia-Echevrria et al. | |
| 2016/0326138 A1* | 11/2016 | Chen .................... | A61K 31/555 |
| 2017/0174687 A1 | 6/2017 | Chen | |
| 2017/0182027 A1 | 6/2017 | Wang | |
| 2017/0304290 A1 | 10/2017 | Wang et al. | |
| 2018/0201613 A1 | 7/2018 | Chen et al. | |
| 2019/0002435 A1 | 1/2019 | Chen et al. | |
| 2019/0269671 A1 | 9/2019 | Wang et al. | |
| 2019/0298712 A1 | 10/2019 | Wang et al. | |

FOREIGN PATENT DOCUMENTS

| | | |
|---|---|---|
| CN | 101809012 | 8/2010 |
| CN | 102344438 | 2/2012 |
| CN | 103483319 | 1/2014 |
| WO | WO 2006/122806 | 11/2006 |
| WO | WO 2008/112407 | 9/2008 |
| WO | WO 2008/112408 | 9/2008 |
| WO | WO 2009/155527 | 12/2009 |
| WO | WO 2010/105761 | 9/2010 |
| WO | WO 2014/113616 | 7/2014 |
| WO | WO 2016/091168 A1 | 6/2016 |

OTHER PUBLICATIONS

Bello, E. et al., E-3810 Is a Potent Dual Inhibitor of VEGFR and FGFR that Exerts Antitumor Activity in Multiple Preclinical Models, Cancer Research; 71(4), Feb. 15, 2011.
Eskens et al, "Phase I Dose Escalation Study of Telatinib, a Tyrosine Kinase Inhibitor of Vascular Endothelial Growth Factor Receptor 2 and 3, Platelet-Derived Growth Factor Receptor β, and c-Kit, in Patients With Advanced or Metastatic Solid Tumors." Journal of Clinical Oncology (2009), vol. 27 (25), pp. 4169-4176.
Han et al., "Anlotinib as a third-line therapy in patients with refractory advanced non-small-cell lung cancer: a multicentre, randomized phase 11 trial (Al TER0302)", 2018, British Journal of Cancer, 118(5), pp. 654-661. (Year: 2018).
Moreno et al., "Tyrosine Kinase Inhibitors in Treating Soft Tissue Sarcomas: sunitinib in non-GIST sarcomas," Clin Transl Oncol (2010) 12:468-472.
National Center for Biotechnology Information. PubChem Compound Database; CI D=25017 411, https://pubchem.ncbi .nlm.nih .gov/compound/25017 411 (accessed Apr. 4, 2018). (Year: 2018).
Sala, F. et al., Development and validation of a high-performance liquid chromatography—tandem mass spectrometry method for the determination of the novel inhibitor of angiogenesis E-3810 in human plasma and its application in a clinical pharmacokinetic study, Journal of Mass Spectrometry, 2011, 46, pp. 1039-1045.

(Continued)

*Primary Examiner* — Sahar Javanmard
(74) *Attorney, Agent, or Firm* — Knobe, Martens, Olson & Bear, LLP

(57) ABSTRACT

Provided in the present invention is a quinoline derivative for treating gastric cancer. 1-[[[4-(4-fluoro-2-methyl-1H-indol-5-yl)oxy-6-methoxyquinolin-7-yl]oxy]methyl]cyclopropylamine or a pharmaceutically acceptable salt, a hydrate or a prodrug thereof as provided in the present application can effectively treat gastric cancer, and can stabilize or relieve the state of illness of a gastric cancer patient.

13 Claims, No Drawings

(56) References Cited

OTHER PUBLICATIONS

Sun et al., "Safety, pharmacokinetics, and antitumor properties of anlotinib, an oral multi-target tyrosine kinase inhibitor, in patients with advanced refractory solid tumors", 2016, Journal of Hematology & Oncology, 9: 105; DOI 10.1186/s 13045-016-0332-8. (Year: 2016).

Traina et al.—Optimizing Chemotherapy Dose and Schedule by Norton-Simon Mathematical Modeling, Breast Dis (2010), vol. 31(1), pp. 1-21.

Xeloda® Prescribing Information; Genentech USA, Inc.,—Xeloda, Mar. 2015.

Zhou, Y. et al., AL3810, a multi-tyrosine kinase inhibitor, exhibits potent anti-angiogenic and ant-tumor activity via targeting VEGFR, FGFR, and PDGFR, Journal of Cellular and Molecular Medicine, vol. 16, No. 10, 2012 pp. 2321-2330.

Silverman, R. "The Organic Chemistry of Drug Design and Drug Action," 2004, Elsevier, pp. 29-32.

Ranson et al, British Journal of Cancer (2004), vol. 90, pp. 2250-2255. (Year: 2004).

Zhang et al., Mol Neurobiol, 2015, vol. 52, pp. 1527-1539. (Year:2015).

* cited by examiner

QUINOLINE DERIVATIVE FOR TREATING GASTRIC CANCER

CROSS-REFERENCE TO RELATED APPLICATIONS

The present application is the U.S. National Phase of International Application PCT/CN2017/080563, filed Apr. 14, 2017, which claims the benefit of priority to Chinese Patent Application No. 201610238157.7, filed Apr. 15, 2016, the disclosures of each of which are hereby incorporated by reference in their entireties.

FIELD OF THE INVENTION

The present invention relates to the field of medical technology, and the present application relates to the use of quinoline derivatives for the treatment of gastric cancer.

BACKGROUND OF THE INVENTION

Gastric cancer originates in the mucosal epithelial cells of the innermost layer of gastric wall, and it can occur in various parts of the stomach, such as gastric antrum, lesser curvature and the anterior and posterior walls thereof, fundus and cardia of the stomach, gastric body, gastroesophageal junction and the like. There are many forms of gastric cancer observed by the naked eye or gastroscope, such as superficial type, mass type, ulcerative type, invasive type, and ulcer cancer (which means carcinogenesis of chronic gastric ulcer). Microscopically, there are many types of cancer cells by histological classification. For example, the World Health Organization (WHO) classifies gastric cancer into adenocarcinoma (including papillary adenocarcinoma, tubular adenocarcinoma, mucinous adenocarcinoma, and signet ring cell carcinoma (also called mucinous cancer)), adenosquamous carcinoma, squamous cell carcinoma, carcinoid tumors, undifferentiated carcinoma, and unclassified carcinoma by histological classification. China divides gastric cancer into adenocarcinoma (including papillary adenocarcinoma, tubular adenocarcinoma, and mucinous adenocarcinoma), signet ring cell carcinoma (also called mucinous carcinoma), undifferentiated carcinoma, special types of cancer (including adenosquamous carcinoma, squamous cell carcinoma, carcinoid tumors, unclassified carcinoma and mixed type carcinoma), among which, adenocarcinoma accounts for approximately 90%.

Surgical treatment, radiation therapy, targeted therapy, chemotherapy and immunotherapy are often used in treating gastric cancer. In recent years, the number of new cases of gastric cancer in China has ranked first in the world. And nearly 50% of new cases of gastric cancer in the world come from China. Gastric cancer is one of the most common malignant tumors in China, and mortality accounts for the first death of malignant tumors in China. Therefore, it is necessary to develop drugs that can effectively treat gastric cancer.

SUMMARY OF THE INVENTION

In a first aspect, the present application provides a method for treating gastric cancer, the method comprising administering a therapeutically effective amount of Compound I or a pharmaceutically acceptable salt thereof to a patient in need of treatment.

The chemical name of Compound I is 1-[[[4-(4-fluoro-2-methyl-1H-indol-5-yl)oxy-6-methoxyquinolin-7-yl]oxy]methyl]cyclopropylamine, which has the following structural formula:

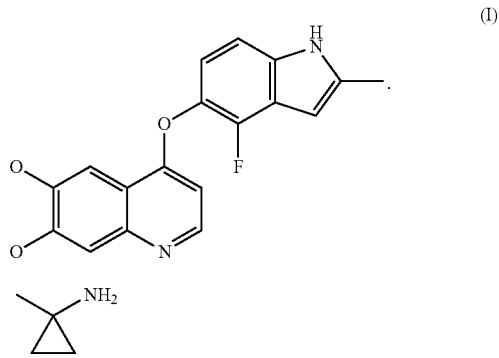

In a second aspect, the present application provides a use of Compound I or a pharmaceutically acceptable salt thereof, for the manufacture of a medicament for treating gastric cancer.

In a third aspect, the present application provides a compound I or a pharmaceutical composition for treating gastric cancer, the pharmaceutical composition comprises Compound I or a pharmaceutically acceptable salt thereof, and at least one pharmaceutically acceptable carrier.

In a fourth aspect, the present application provides a kit for treating gastric cancer, comprising: (a) at least one unit dosage form of a pharmaceutical composition of Compound I or a pharmaceutically acceptable salt thereof, and (b) instructions for treating gastric cancer.

DETAILED EMBODIMENTS OF THE INVENTION

In a first aspect, the present application provides a method of treating gastric cancer, which comprises administering to a patient in need of treatment a therapeutically effective amount of Compound I or a pharmaceutically acceptable salt thereof. In some typical embodiments, the gastric cancer is advanced and/or metastatic gastric cancer; in some more typical embodiments, the gastric cancer is advanced and/or metastatic gastric cancer after failure of treatment with taxanes antineoplastic agents, camptothecins antineoplastic agents, adriamycins antineoplastic agents, platinum complexes and/or fluoropyrimidine derivatives. In some typical embodiments, the gastric cancer is a moderately differentiated or poorly differentiated gastric cancer. In some embodiments of the present application, a method for treating gastric adenocarcinoma is provided, comprising administering to a patient in need of treatment a therapeutically effective amount of Compound I or a pharmaceutically acceptable salt thereof, wherein the gastric adenocarcinoma includes but not limited to papillary adenocarcinoma, tubular adenocarcinoma, mucinous adenocarcinoma, signet ring cell carcinoma, or a mixed-type adenocarcinoma of the above histological types. In some typical embodiments, the gastric adenocarcinoma is advanced and/or metastatic gastric adenocarcinoma; in some more typical embodiments, the gastric adenocarcinoma is advanced and/or metastatic gastric adenocarcinoma after failure of treatment with taxanes antineoplastic agents, camptothecins antineoplastic agents, adriamycins antineoplastic agents, platinum complexes and/or fluoropyrimidine derivatives. In some typical embodiments, the gastric adenocarcinoma is a moderately differentiated or poorly differentiated gastric adenocarcinoma.

In some embodiments of the present application, a method for treating papillary adenocarcinoma is provided, comprising administering to a patient in need of treatment a therapeutically effective amount of Compound I or a pharmaceutically acceptable salt thereof. In some typical embodiments, the papillary adenocarcinoma is advanced and/or metastatic papillary adenocarcinoma; in some more typical embodiments, the papillary adenocarcinoma is advanced and/or metastatic papillary adenocarcinoma after failure of treatment with taxanes antineoplastic agents, camptothecins antineoplastic agents, adriamycins antineoplastic agents, platinum complexes and/or fluoropyrimidine derivatives. In some typical embodiments, the papillary adenocarcinoma is a moderately differentiated or poorly differentiated papillary adenocarcinoma.

In some embodiments of the present application, a method for treating tubular adenocarcinoma is provided, comprising administering to a patient in need of treatment a therapeutically effective amount of Compound I or a pharmaceutically acceptable salt thereof. In some typical embodiments, the tubular adenocarcinoma is advanced and/or metastatic tubular adenocarcinoma; in some more typical embodiments, the tubular adenocarcinoma is advanced and/or metastatic tubular adenocarcinoma after failure treatment with taxanes antineoplastic agents, camptothecins antineoplastic agents, adriamycins antineoplastic agents, platinum complexes and/or fluoropyrimidine derivatives. In some typical embodiments, the tubular adenocarcinoma is a moderately differentiated or poorly differentiated tubular adenocarcinoma.

In some embodiments of the present application, a method for treating mucinous adenocarcinoma is provided, comprising administering to a patient in need of treatment a therapeutically effective amount of Compound I or a pharmaceutically acceptable salt thereof. In some typical embodiments, the mucinous adenocarcinoma is advanced and/or metastatic mucinous adenocarcinoma; in some more typical embodiments, the mucinous adenocarcinoma is advanced and/or metastatic mucinous adenocarcinoma after failure of treatment with taxanes antineoplastic agents, camptothecins antineoplastic agents, adriamycins antineoplastic agents, platinum complexes and/or fluoropyrimidine derivatives. In some typical embodiments, the mucinous adenocarcinoma is a moderately differentiated or poorly differentiated mucinous adenocarcinoma.

In some embodiments of the present application, a method for treating signet ring cell carcinoma is provided, comprising administering to a patient in need of treatment a therapeutically effective amount of Compound I or a pharmaceutically acceptable salt thereof. In some typical embodiments, the signet ring cell carcinoma is advanced and/or metastatic signet ring cell carcinoma; in some more typical embodiments, the signet ring cell carcinoma is advanced and/or metastatic signet ring cell carcinoma after failure of treatment with taxanes antineoplastic agents, camptothecins antineoplastic agents, adriamycins antineoplastic agents, platinum complexes and/or fluoropyrimidine derivatives.

In some embodiments of the present application, a method for treating gastroesophageal junction adenocarcinoma is provided, comprising administering to a patient in need of treatment a therapeutically effective amount of Compound I or a pharmaceutically acceptable salt thereof. In some typical embodiments, the gastroesophageal junction adenocarcinoma is advanced and/or metastatic gastroesophageal junction adenocarcinoma; in some more typical embodiments, the gastroesophageal junction adenocarcinoma is advanced and/or metastatic gastroesophageal junction adenocarcinoma after failure treatment with taxanes antineoplastic agents, camptothecins antineoplastic agents, adriamycins antineoplastic agents, platinum complexes and/or fluoropyrimidine derivatives. In some typical embodiments, the gastroesophageal junction adenocarcinoma is a moderately differentiated or poorly differentiated gastroesophageal junction adenocarcinoma.

In some embodiments of the present application, the taxanes antineoplastic agents include but not limited to paclitaxel and docetaxel; the camptothecins antineoplastic agents include but not limited to irinotecan; the adriamycins antineoplastic agents include but not limited to epirubicin; the platinum complexes include, but not limited to, one or more of cisplatin, carboplatin, nedaplatin and oxaliplatin; In some embodiments, the fluoropyrimidine derivatives include, but not limited to, one or more of capecitabine, fluorouracil, tegadifur, deoxyfluorouridine, tegafur and carmofur.

Compound I can be administered in the free base formor in the form of salts, hydrates and prodrugs thereof, wherein the prodrug is converted to the free base form of Compound I in vivo. For example, a pharmaceutically acceptable salt of Compound I is within the scope of this application, and the salts can be produced from different organic and inorganic acids by methods well known in the art.

In some embodiments, the Compound I is administered in the form of hydrochlorides thereof. In some embodiments, Compound I is administered in the form of monohydrochloride thereof. In some embodiments, Compound I is administered in the form of dihydrochloride thereof. In some embodiments, Compound I is administered in the crystalline form of hydrochlorides thereof. In a specific embodiment, Compound I is administered in the crystalline form of dihydrochloride thereof.

Compound I or the pharmaceutically acceptable salt thereof can be administered by a variety of routes including, but not limited to, those selected from the group consisting of oral, parenteral, intraperitoneal, intravenous, intraarterial, transdermal, sublingual, intramuscular, rectal, transbuccal, intranasal, inhalative, vaginal, intraocular, topical, subcutaneous, intrafat, intraarticular, intraperitoneal, and intrathecal routes. In some specific embodiments, it is administered orally.

The amount of Compound I or the pharmaceutically acceptable salt thereof can be determined based on the severity of the disease, the response to the disease, any treatment-related toxicity, and the age and health status of the patient. In some embodiments, the daily dosage of Compound I or the pharmaceutically acceptable salt thereof is 2 mg-20 mg. In some embodiments, the daily dosage of Compound I or the pharmaceutically acceptable salt thereof is 5 mg-20 mg. In some embodiments, the daily dosage of Compound I or the pharmaceutically acceptable salt thereof is 8 mg-20 mg. In some embodiments, the daily dosage of Compound I or the pharmaceutically acceptable salt thereof is 10 mg-16 mg. In some embodiments, the daily dosage of Compound I or the pharmaceutically acceptable salt thereof is 10 mg-14 mg. In some specific embodiments, the daily dosage of Compound I or the pharmaceutically acceptable salt thereof is 10 mg. In some specific embodiments, the daily dosage of Compound I or the pharmaceutically acceptable salt thereof is 12 mg. In some specific embodiments, the daily dosage of Compound I or the pharmaceutically acceptable salt thereof is 14 mg. In some specific embodiments, the daily dosage of Compound I or the pharmaceutically acceptable salt thereof is 16 mg.

Compound I or the pharmaceutically acceptable salt thereof can be administered one or more times a day. In some embodiments, Compound I or the pharmaceutically acceptable salt thereof is administered once a day. In some embodiments, Compound I or the pharmaceutically acceptable salt thereof can be administered once a day in the form of oral solid preparation.

The method of administration can be generally determined according to the activity and toxicity of drugs as well as tolerability of patients and the like. Preferably, Compound I or the pharmaceutically acceptable salt thereof is administered at intervals, which includes the dosing periods and rest periods, the compound I or the pharmaceutically acceptable salt thereof may be administered once or more times a day during the dosing periods. For example, during the dosing period, administration of Compound I or the pharmaceutically acceptable salt thereof is performed each day and then stopped for a period of time during the rest period, followed by dosing period, and then rest period, which can be repeated several times. The ratio of the dosing period to the rest period by the day is 2:0.5-5, preferably 2:0.5-3, more preferably 2:0.5-2, further preferably 2:0.5-1.

In some embodiments, the administration is continuously performed for 2 weeks and stopped for 2 weeks. In some embodiments, the administration is continuously performed once a day for 14 days, and then stopped for 14 days; followed by administration once a day for 14 days and then rest for 14 days; such interval dosage regimen with two-week dosing period and two-week rest period can be repeated several times.

In some embodiments, the administration is continuously performed for 2 weeks and stopped for 1 week. In some embodiments, the administration is continuously performed once a day for 14 days, and then stopped for 7 days; followed by administration once a day for 14 days and then rest for 7 days; such interval dosage regimen with two-week dosing period and one-week rest period can be repeated several times.

In some embodiments, the administration is continuously performed for 5 days and stopped for 2 days. In some embodiments, the administration is continuously performed once a day for 5 days, and then stopped for 2 days; followed by administration once a day for 5 days and then rest for 2 days; such interval dosage regimen with five-day dosing period and two-day rest period can be repeated several times.

In some embodiments, Compound I or the pharmaceutically acceptable salt thereof is to administered to a gastric cancer patient separately as the sole active ingredient. In some embodiments, Compound I or the pharmaceutically acceptable salt thereof is administered to a gastric cancer patient simultaneously or sequentially with other antitumor drugs. In some embodiments, the other antitumor drugs include, but not limited to, one or more of platinum complexes, fluoropyrimidine derivatives, camptothecin and its derivatives, anthraquinones antitumor antibiotics, taxanes compounds, mitomycin and trastuzumab. In some embodiments, the platinum complexes include, but not limited to, one or more of cisplatin, carboplatin, nedaplatin and oxaliplatin; in some embodiments, the fluoropyrimidine derivatives include, but not limited to, one or more of capecitabine, fluorouracil, tegadifur, deoxyfluorouridine, tegafur and carmofur; in some embodiments, the camptothecin and its derivatives include, but not limited to, one or more of camptothecin, hydroxycamptothecin, irinotecan and topotecan; in some embodiments, the anthraquinones antitumor antibiotics include, but not limited to, one or more of doxorubicin, epirubicin, daunorubicin and mitoxantrone; in some embodiments, the taxanes compounds include, but not limited to, paclitaxel and/or docetaxel.

In a second aspect, the present application provides a use of Compound I or the pharmaceutically acceptable salt thereof in the manufacture of a medicament for treating gastric cancer. In some typical embodiments, the gastric cancer is advanced and/or metastatic gastric cancer; in some more typical embodiments, the gastric cancer is advanced and/or metastatic gastric cancer after failure of treatment with taxanes antineoplastic agents, camptothecins antineoplastic agents, adriamycins antineoplastic agents, platinum complexes and/or fluoropyrimidine derivatives. In some typical embodiments, the gastric cancer is a moderately differentiated or poorly differentiated gastric cancer.

In some embodiments of the present application, a use of Compound I or the pharmaceutically acceptable salt thereof in the manufacture of a medicament for treating gastric adenocarcinoma is provided, wherein the gastric adenocarcinoma includes but not limited to papillary adenocarcinoma, tubular adenocarcinoma, mucinous adenocarcinoma, signet ring cell carcinoma, or a mixed-type adenocarcinoma of the above histological types. In some typical embodiments, the gastric adenocarcinoma is advanced and/or metastatic gastric adenocarcinoma; in some more typical embodiments, the gastric adenocarcinoma is advanced and/or metastatic gastric adenocarcinoma after failure of treatment with taxanes antineoplastic agents, camptothecins antineoplastic agents, adriamycins antineoplastic agents, platinum complexes and/or fluoropyrimidine derivatives. In some typical embodiments, the gastric adenocarcinoma is a moderately differentiated or poorly differentiated gastric adenocarcinoma.

In some embodiments of the present application, a use of Compound I or the pharmaceutically acceptable salt thereof in the manufacture of a medicament for treating papillary adenocarcinoma is provided. In some typical embodiments, the papillary adenocarcinoma is advanced and/or metastatic papillary adenocarcinoma; in some more typical embodiments, the papillary adenocarcinoma is advanced and/or metastatic papillary adenocarcinoma after failure of treatment with taxanes antineoplastic agents, camptothecins antineoplastic agents, adriamycins antineoplastic agents, platinum complexes and/or fluoropyrimidine derivatives. In some typical embodiments, the papillary adenocarcinoma is a moderately differentiated or poorly differentiated papillary adenocarcinoma.

In some embodiments of the present application, a use of Compound I or the pharmaceutically acceptable salt thereof in the manufacture of a medicament for treating tubular adenocarcinoma is provided. In some typical embodiments, the tubular adenocarcinoma is advanced and/or metastatic tubular adenocarcinoma; in some more typical embodiments, the tubular adenocarcinoma is advanced and/or metastatic tubular adenocarcinoma after failure of treatment with taxanes antineoplastic agents, camptothecins antineoplastic agents, adriamycins antineoplastic agents, platinum complexes and/or fluoropyrimidine derivatives. In some typical embodiments, the tubular adenocarcinoma is a moderately differentiated or poorly differentiated tubular adenocarcinoma.

In some embodiments of the present application, a use of Compound I or the pharmaceutically acceptable salt thereof in the manufacture of a medicament for treating mucinous adenocarcinoma is provided. In some typical embodiments, the mucinous adenocarcinoma is advanced and/or metastatic mucinous adenocarcinoma; in some more typical embodiments, the mucinous adenocarcinoma is advanced and/or metastatic mucinous adenocarcinoma after failure of treatment with taxanes antineoplastic agents, camptothecins antineoplastic agents, adriamycins antineoplastic agents, platinum complexes and/or fluoropyrimidine derivatives. In some typical embodiments, the mucinous adenocarcinoma is a moderately differentiated or poorly differentiated mucinous adenocarcinoma.

In some embodiments of the present application, a use of Compound I or the pharmaceutically acceptable salt thereof in the manufacture of a medicament for treating signet ring cell carcinoma is provided. In some typical embodiments, the signet ring cell carcinoma is advanced and/or metastatic signet ring cell carcinoma; in some more typical embodiments, the signet ring cell carcinoma is advanced and/or metastatic signet ring cell carcinoma after failure of treatment with taxanes antineoplastic agents, camptothecins antineoplastic agents, adriamycins antineoplastic agents, platinum complexes and/or fluoropyrimidine derivatives.

In some embodiments of the present application, a use of Compound I or the pharmaceutically acceptable salt thereof in the manufacture of a medicament for treating gastroesophageal junction adenocarcinoma is provided. In some typical embodiments, the gastroesophageal junction adenocarcinoma is advanced and/or metastatic gastroesophageal junction adenocarcinoma; in some more typical embodiments, the gastroesophageal junction adenocarcinoma is advanced and/or metastatic gastroesophageal junction adenocarcinoma after failure of treatment with taxanes antineoplastic agents, camptothecins antineoplastic agents, adriamycins antineoplastic agents, platinum complexes and/or fluoropyrimidine derivatives. In some typical embodiments, the gastroesophageal junction adenocarcinoma is a moderately differentiated or poorly differentiated gastroesophageal junction adenocarcinoma.

In some embodiments of the present application, the taxanes antineoplastic agents include but not limited to paclitaxel and docetaxel; the camptothecins antineoplastic agents include but not limited to irinotecan; the adriamycins antineoplastic agents include but not limited to epirubicin; the platinum complexes include, but not limited to, one or more of cisplatin, carboplatin, nedaplatin and oxaliplatin; In some embodiments, the fluoropyrimidine derivatives include, but not limited to, one or more of capecitabine, fluorouracil, tegadifur, deoxyfluorouridine, tegafur and carmofur.

Compound I can be in the form of free base or salts, hydrates and prodrugs thereof, wherein the prodrug is converted to the free base form of Compound I in vivo. For example, a pharmaceutically acceptable salt of Compound I is within the scope of this application, which can be produced from different organic and inorganic acids by methods well known in the art.

In some embodiments, the Compound I or the pharmaceutically acceptable salts thereof is hydrochlorides of Compound I. In some embodiments, Compound I or the pharmaceutically acceptable salts thereof is monohydrochloride of Compound I. In some embodiments, Compound I or the pharmaceutically acceptable salts thereof is dihydrochloride of Compound I. In some embodiments, Compound I or the pharmaceutically acceptable salts thereof is in the crystalline form of hydrochlorides of Compound I. In a specific embodiment, Compound I or the pharmaceutically acceptable salts thereof is in the crystalline form of dihydrochloride of Compound I.

The amount of Compound I or the pharmaceutically acceptable salt thereof can be determined based on the severity of the disease, the response to the disease, any treatment-related toxicity, and the age and health condition of the patient. In some embodiments, the administered daily dosage of Compound I or the pharmaceutically acceptable salt thereof is 2 mg-20 mg. In some embodiments, the administered daily dosage of Compound I or the pharmaceutically acceptable salt thereof is 5 mg-20 mg. In some embodiments, the amount of Compound I or the pharmaceutically acceptable salt thereof is 8 mg-20 mg. In some embodiments, the amount of Compound I or the pharmaceutically acceptable salt thereof is 10 mg-16 mg. In some embodiments, the amount of Compound I or the pharmaceutically acceptable salt thereof is 10 mg-14 mg. In some specific embodiments, the amount of Compound I or the pharmaceutically acceptable salt thereof is 10 mg. In some specific embodiments, the amount of Compound I or the pharmaceutically acceptable salt thereof is 12 mg. In some specific embodiments, the amount of Compound I or the pharmaceutically acceptable salt thereof is 14 mg. In some specific embodiments, the amount of Compound I or the pharmaceutically acceptable salt thereof is 16 mg.

In some embodiments, a use of Compound I or the pharmaceutically acceptable salt thereof as the sole active ingredient for the manufacture of a medicament for treating gastric cancer is provided. In some embodiments, a use of Compound I or the pharmaceutically acceptable salt thereof and other antitumor drugs as active ingredients for the manufacture of a medicament for treating gastric cancer is provided. In some embodiments, the other antitumor drugs include, but not limited to, one or more of platinum complexes, fluoropyrimidine derivatives, camptothecin and its derivatives, anthraquinones antitumor antibiotics, taxanes, mitomycin and trastuzumab. In some embodiments, the platinum complexes include, but not limited to, one or more of cisplatin, carboplatin, nedaplatin and oxaliplatin; in some embodiments, the fluoropyrimidine derivatives include, but not limited to, one or more of capecitabine, fluorouracil, tegadifur, deoxyfluorouridine, tegafur and carmofur in some embodiments, the camptothecin and its derivatives include, but not limited to, one or more of camptothecin, hydroxycamptothecin, irinotecan and topotecan; in some embodiments, anthraquinones antitumor antibiotics include, but not limited to, one or more of doxorubicin, epirubicin, daunorubicin and mitoxantrone; in some embodiments, the taxanes include, but not limited to, paclitaxel and/or docetaxel.

In a third aspect, the present application provides Compound I or a pharmaceutical composition comprising Compound I or the pharmaceutically acceptable salt thereof and at least one pharmaceutically acceptable carrier for treating gastric cancer. In some typical embodiments, the gastric cancer is advanced and/or metastatic gastric cancer; in some more typical embodiments, the gastric cancer is advanced and/or metastatic gastric cancer after failure of treatment with taxanes antineoplastic agents, camptothecins antineoplastic agents, adriamycins antineoplastic agents, platinum complexes and/or fluoropyrimidine derivatives. In some typical embodiments, the gastric cancer is a moderately differentiated or poorly differentiated gastric cancer.

In some embodiments of the present application, Compound I or a pharmaceutical composition for treating gastric adenocarcinoma is provided, wherein the pharmaceutical composition comprises Compound I or the pharmaceutically acceptable salt thereof and at least one pharmaceutically acceptable carrier. The gastric adenocarcinoma includes but not limited to papillary adenocarcinoma, tubular adenocarcinoma, mucinous adenocarcinoma, signet ring cell carcinoma, or a mixed-type adenocarcinoma of the above histological types. In some typical embodiments, the gastric adenocarcinoma is advanced and/or metastatic gastric adenocarcinoma; in some more typical embodiments, the gastric adenocarcinoma is advanced and/or metastatic gastric adenocarcinoma after failure of treatment with taxanes antineoplastic agents, camptothecins antineoplastic agents, adriamycins antineoplastic agents, platinum complexes and/or fluoropyrimidine derivatives. In some typical embodiments, the gastric adenocarcinoma is a moderately differentiated or poorly differentiated gastric adenocarcinoma.

In some embodiments of the present application, Compound I or a pharmaceutical composition for treating papillary adenocarcinoma is provided, wherein the pharmaceutical composition comprises Compound I or the pharmaceutically acceptable salt thereof and at least one pharmaceutically acceptable carrier. In some typical embodiments, the papillary adenocarcinoma is advanced and/or metastatic papillary adenocarcinoma; in some more typical embodiments, the papillary adenocarcinoma is advanced and/or metastatic papillary adenocarcinoma after failure of treatment with taxanes antineoplastic agents, camptothecins antineoplastic agents, adriamycins antineoplastic agents, platinum complexes and/or fluoropyrimidine derivatives. In some typical embodiments, the papillary adenocarcinoma is a moderately differentiated or poorly differentiated papillary adenocarcinoma.

In some embodiments of the present application, Compound I or a pharmaceutical composition for treating tubular adenocarcinoma is provided, wherein the pharmaceutical composition comprises Compound I or the pharmaceutically acceptable salt thereof and at least one pharmaceutically acceptable carrier. In some typical embodiments, the tubular adenocarcinoma is advanced and/or metastatic tubular adenocarcinoma; in some more typical embodiments, the tubular adenocarcinoma is advanced and/or metastatic tubular adenocarcinoma after failure of treatment with taxanes antineoplastic agents, camptothecins antineoplastic agents, adriamycins antineoplastic agents, platinum complexes and/or fluoropyrimidine derivatives. In some typical embodiments, the tubular adenocarcinoma is a moderately differentiated or poorly differentiated tubular adenocarcinoma.

In some embodiments of the present application, Compound I or a pharmaceutical composition for treating mucinous adenocarcinoma is provided, wherein the pharmaceutical composition comprises Compound I or the pharmaceutically acceptable salt thereof and at least one pharmaceutically acceptable carrier. In some typical embodiments, the mucinous adenocarcinoma is advanced and/or metastatic mucinous adenocarcinoma; in some more typical embodiments, the mucinous adenocarcinoma is advanced and/or metastatic mucinous adenocarcinoma after failure of treatment with taxanes antineoplastic agents, camptothecins antineoplastic agents, adriamycins antineoplastic agents, platinum complexes and/or fluoropyrimidine derivatives. In some typical embodiments, the mucinous adenocarcinoma is a moderately differentiated or poorly differentiated mucinous adenocarcinoma.

In some embodiments of the present application, Compound I or a pharmaceutical composition for treating signet ring cell carcinoma is provided, wherein the pharmaceutical composition comprises Compound I or the pharmaceutically acceptable salt thereof and at least one pharmaceutically acceptable carrier. In some typical embodiments, the signet ring cell carcinoma is advanced and/or metastatic signet ring cell carcinoma; in some more typical embodiments, the signet ring cell carcinoma is advanced and/or metastatic signet ring cell carcinoma after failure of treatment with taxanes antineoplastic agents, camptothecins antineoplastic agents, adriamycins antineoplastic agents, platinum complexes and/or fluoropyrimidine derivatives.

In some embodiments of the present application, Compound I or a pharmaceutical composition for treating gastroesophageal junction adenocarcinoma is provided, wherein the pharmaceutical composition comprises Compound I or the pharmaceutically acceptable salt thereof and at least one pharmaceutically acceptable carrier. In some typical embodiments, the gastroesophageal junction adenocarcinoma advanced and/or metastatic gastroesophageal junction adenocarcinoma; in some more typical embodiments, the gastroesophageal junction adenocarcinoma is advanced and/or metastatic gastroesophageal junction adenocarcinoma after failure of treatment with taxanes antineoplastic agents, camptothecins antineoplastic agents, adriamycins antineoplastic agents, platinum complexes and/or fluoropyrimidine derivatives. In some typical embodiments, the gastroesophageal junction adenocarcinoma is a moderately differentiated or poorly differentiated gastroesophageal junction adenocarcinoma.

In some embodiments of the present application, the taxanes antineoplastic agents include but not limited to paclitaxel and docetaxel; the camptothecins antineoplastic agents include but not limited to irinotecan; the adriamycins antineoplastic agents include but not limited to epirubicin; the platinum complexes include, but not limited to, one or more of cisplatin, carboplatin, nedaplatin and oxaliplatin; In some embodiments, the fluoropyrimidine derivatives include, but not limited to, one or more of capecitabine, fluorouracil, tegadifur, deoxyfluorouridine, tegafur and carmofur. Compound I can be in the form of free base or salts, hydrates and prodrugs thereof, wherein the prodrug is converted to the free base form of Compound I in vivo. For example, a pharmaceutically acceptable salt of Compound I is within the scope of this application, which can be produced from different organic and inorganic acids by methods well known in the art.

In some embodiments, Compound I or the pharmaceutically acceptable salt thereof is in the form of hydrochlorides of Compound I. In some embodiments, Compound I or the pharmaceutically acceptable salt thereof is in the form of monohydrochloride of Compound I. In some embodiments, Compound I or the pharmaceutically acceptable salt thereof is in the form of dihydrochloride of Compound I. In some embodiments, Compound I or the pharmaceutically acceptable salt thereof is in the crystalline form of hydrochlorides of Compound I. In a specific embodiment, Compound I or the pharmaceutically acceptable salt thereof is in the crystalline form of dihydrochloride of Compound I.

The administered dosage of Compound I or the pharmaceutically acceptable salt thereof can be determined based on the severity of the disease, the response to the disease, any treatment-related toxicity, and the age and health condition of the patient. In some embodiments, the administered daily dosage of Compound I or the pharmaceutically acceptable salt thereof is 2 mg-20 mg. In some embodiments, the administered daily dosage of Compound I or the pharmaceutically acceptable salt thereof is 5 mg-20 mg. In some embodiments, the amount of Compound I or the pharmaceutically acceptable salt thereof in the pharmaceutical composition is 8 mg-20 mg. In some embodiments, the amount of Compound I or the pharmaceutically acceptable salt thereof is 10 mg-16 mg. In some embodiments, the amount of Compound I or the pharmaceutically acceptable salt thereof is 10 mg-14 mg. In some specific embodiments, the amount of Compound I or the pharmaceutically acceptable salt thereof is 10 mg. In some specific embodiments, the amount of Compound I or the pharmaceutically acceptable salt thereof is 12 mg. In some specific embodiments, the amount of Compound I or the pharmaceutically acceptable salt thereof is 14 mg. In some specific embodiments, the amount of Compound I or the pharmaceutically acceptable salt thereof is 16 mg.

In some embodiments of the present application, the pharmaceutical composition is a formulation suitable for oral administration, including tablets, capsules, powders, granules, pills, pastes, pulvis and the like, tablets and capsules are preferred. The tablets may be conventional tablets, dispersible tablets, effervescent tablets, sustained release tablets, controlled release tablets or enteric coated tablets, and the capsules may be conventional capsules, sustained release capsules, controlled release capsules or enteric capsules. The oral preparation can be prepared by conventional methods using pharmaceutically acceptable carriers well known in the art. Pharmaceutically acceptable carriers include fillers, absorbents, wetting agents, binders, disintegrants, lubricants and the like. Fillers include starch, lactose, mannitol, microcrystalline cellulose, etc.; absorbents include calcium sulfate, calcium hydrogen phosphate, calcium carbonate, etc.; wetting agents include water, ethanol, etc.; binders include hypromellose, povidone, microcrystalline cellulose, etc.; disintegrants include croscarmellose sodium, crospovidone, surfactant, low-substituted hydroxypropyl cellulose, etc.; lubricants include magnesium stearate, talc, polyethylene glycol, sodium dodecyl sulfate, colloidal silicon dioxide, and the like. Pharmaceutical excipients also include coloring agents, sweeteners and the like.

In some embodiments, the pharmaceutical composition is a solid formulation suitable for oral administration. The composition may be in the form of, for example, tablets or capsules. In some specific embodiments, the pharmaceutical composition is capsules. In some specific embodiments of the present application, the pharmaceutically acceptable carriers of the oral solid preparation include mannitol, microcrystalline cellulose, hydroxypropylcellulose, and magnesium stearate.

In some embodiments, a pharmaceutical composition formulated into a unit dosage form for treating gastric cancer is provided. In some embodiments, the pharmaceutical composition formulated into a unit dosage form contains 2 mg-20 mg of Compound I or the pharmaceutically acceptable salt thereof. In some embodiments, the pharmaceutical composition formulated into a unit dosage form contains 5 mg-20 mg of Compound I or the pharmaceutically acceptable salt thereof. In some embodiments, the pharmaceutical composition formulated into a unit dosage form contains 8 mg-20 mg of Compound I or the pharmaceutically acceptable salt thereof, preferably 10 mg-16 mg of Compound I or the pharmaceutically acceptable salt thereof, more preferably, 10 mg-14 mg of the Compound I or the pharmaceutically acceptable salt thereof. In some specific embodiments, the pharmaceutical composition formulated into a unit dosage form contains 10 mg of Compound I or the pharmaceutically acceptable salt thereof. In some specific embodiments, the pharmaceutical composition formulated into a unit dosage form contains 12 mg of Compound I or the pharmaceutically acceptable salt thereof. In some specific embodiments, the pharmaceutical composition formulated into a unit dosage form contains 14 mg of Compound I or the pharmaceutically acceptable salt thereof. In some specific embodiments, the pharmaceutical composition formulated into a unit dosage form contains 16 mg of Compound I or the pharmaceutically acceptable salt thereof. For example, for tablets or capsules, "a pharmaceutical composition formulated into a unit dosage form" means every one tablet or every one capsule.

Preferably, the pharmaceutical composition above mentioned is administered at intervals. The interval dosage regimen includes the dosing periods and rest periods, and pharmaceutical composition above mentioned may be administered once or more times a day during the dosing periods. For example, during the dosing period, administration of the pharmaceutical composition is performed each day and then stopped for a period of time during the rest period, followed by dosing period, and then rest period, which can be repeated several times. The ratio of dosing period to rest period by the day is 2:0.5-5, preferably 2:0.5-3, more preferably 2:0.5-2, further preferably 2:0.5-1.

In some embodiments, the administration is continuously performed for 2 weeks and stopped for 2 weeks. In some embodiments, the administration is continuously performed once a day for 14 days, and then stopped for 14 days; followed by administration once a day for 14 days and then rest for 14 days; such interval dosage regimen with two-week dosing period and two-week rest period can be repeated several times.

In some embodiments, the administration is continuously performed for 2 weeks and stopped for 1 week. In some embodiments, the administration is continuously performed once a day for 14 days, and then stopped for 7 days; followed by administration once a day for 14 days and then rest for 7 days; such interval dosage regimen with two-week dosing period and one-week rest period can be repeated several times.

In some embodiments, the administration is continuously performed for 5 days and then stopped for 2 days. In some embodiments, the administration is performed once a day for 5 days, and then stopped for 2 days; followed by administration once a day for 5 days and then rest for 2 days; such interval dosage regimen with five-day dosing period and two-day rest period can be repeated several times.

In some embodiments, a pharmaceutical composition for treating gastric cancer is provided, wherein the pharmaceutical composition comprises Compound I or the pharmaceutically acceptable salt thereof as the sole active ingredient. In some embodiments, the pharmaceutical composition provided further comprises other antitumor drugs. In some embodiments, the other antitumor drugs include, but not limited to, one or more of platinum complexes, fluoropyrimidine derivatives, camptothecin and its derivatives, anthraquinones antitumor antibiotics, taxanes, mitomycin and trastuzumab. In some embodiments, the platinum complexes include, but not limited to, one or more of cisplatin, carboplatin, nedaplatin and oxaliplatin; in some embodiments, the fluoropyrimidine derivatives include, but not limited to, one or more of capecitabine, fluorouracil, tegadifur, deoxyfluorouridine, tegafur and carmofur; in some embodiments, the camptothecin and its derivatives include, but not limited to, one or more of camptothecin, hydroxycamptothecin, irinotecan and topotecan; in some embodiments, the anthraquinones antitumor antibiotics include, but not limited to, one or more of doxorubicin, epirubicin, daunorubicin and mitoxantrone; in some embodiments, the taxanes include, but not limited to paclitaxel and/or docetaxel.

In another aspect, the present application further provides a kit for treating gastric cancer, comprising: (a) at least one unit dosage form of a pharmaceutical composition of Compound I or the pharmaceutically acceptable salt thereof, and (b) instructions for treating gastric cancer. In some embodiments, a kit comprising: (a) at least one unit dosage form of oral formulation of Compound I or the pharmaceutically acceptable salt thereof, and (b) interval dosage regimen instructions for treating gastric cancer is provided. In some specific embodiments, a kit comprising: (a) at least one unit dosage form of tablets or capsules of Compound I or the pharmaceutically acceptable salt thereof, and (b) interval dosage regimen instructions for treating gastric cancer is provided.

In some embodiments, the gastric cancer is advanced and/or metastatic gastric cancer; in some typical embodiments, the gastric cancer is advanced and/or metastatic gastric cancer after failure of treatment with taxanes antineoplastic agents, camptothecins antineoplastic agents, adriamycins antineoplastic agents, platinum complexes and/or fluoropyrimidine derivatives. In some typical embodiments, the gastric cancer is a moderately differentiated or poorly differentiated gastric cancer.

In some embodiments of the present application, the gastric cancer is gastric adenocarcinoma; in some typical embodiments, the gastric adenocarcinoma is advanced and/or metastatic gastric adenocarcinoma after failure of treatment with taxanes antineoplastic agents, camptothecins antineoplastic agents, adriamycins antineoplastic agents, platinum complexes and/or fluoropyrimidine derivatives. In some typical embodiments, the gastric adenocarcinoma is a moderately differentiated or poorly differentiated gastric adenocarcinoma.

In some embodiments of the present application, the gastric adenocarcinoma includes but not limited to papillary adenocarcinoma, tubular adenocarcinoma, mucinous adenocarcinoma, signet ring cell carcinoma, or a mixed-type adenocarcinoma of the above histological types; in some typical embodiments, the gastric adenocarcinoma is advanced and/or metastatic papillary adenocarcinoma, tubular adenocarcinoma, mucinous adenocarcinoma, signet ring cell carcinoma, or a mixed-type adenocarcinoma of the above histological types after failure of treatment with taxanes antineoplastic agents, camptothecins antineoplastic agents, adriamycins antineoplastic agents, platinum complexes and/or fluoropyrimidine derivatives. In some typical embodiments, the gastric adenocarcinoma is a moderately differentiated or poorly differentiated papillary adenocarcinoma, tubular adenocarcinoma, mucinous adenocarcinoma, or a mixed-type adenocarcinoma of the above histological types.

In some embodiments of the present application, the gastric cancer is gastroesophageal junction adenocarcinoma; in some typical embodiments, the gastroesophageal junction adenocarcinoma is advanced and/or metastatic gastroesophageal junction adenocarcinoma after failure of treatment with taxanes antineoplastic agents, camptothecins antineoplastic agents, adriamycins antineoplastic agents, platinum complexes and/or fluoropyrimidine derivatives.

The tablets may be conventional tablets, dispersible tablets, effervescent tablets, sustained release tablets, controlled release tablets or enteric coated tablets, and the capsules may be conventional capsules, sustained release capsules, controlled release capsules or enteric capsules. The oral formulation can be prepared by conventional methods using pharmaceutically acceptable carriers well known in the art. Pharmaceutically acceptable carriers include fillers, absorbents, wetting agents, binders, disintegrants, lubricants and the like. Fillers include starch, lactose, mannitol, microcrystalline cellulose, etc.; absorbents include calcium sulfate, calcium hydrogen phosphate, calcium carbonate, etc.; wetting agents include water, ethanol, etc.; binders include hypromellose, povidone, microcrystalline cellulose, etc.; disintegrants include croscarmellose sodium, crospovidone, surfactant, low-substituted hydroxypropyl cellulose, etc.; lubricants include magnesium stearate, talc, polyethylene glycol, sodium dodecyl sulfate, colloidal silicon dioxide, and the like. Pharmaceutical excipients also include coloring agents, sweeteners and the like.

In some embodiments, the pharmaceutical composition formulated into a unit dosage form contains 2 mg-20 mg of Compound I or the pharmaceutically acceptable salt thereof. In some embodiments, the pharmaceutical composition formulated into a unit dosage form contains 5 mg-20 mg of Compound I or the pharmaceutically acceptable salt thereof. In some embodiments, the pharmaceutical composition formulated into a unit dosage form contains 8 mg-20 mg of Compound I or the pharmaceutically acceptable salt thereof, preferably 10 mg-16 mg of Compound I or the pharmaceutically acceptable salt thereof, more preferably, 10 mg-14 mg of Compound I or the pharmaceutically acceptable salt thereof. In some specific embodiments, the pharmaceutical composition formulated into a unit dosage form contains 10 mg of Compound I or the pharmaceutically acceptable salt thereof. In some specific embodiments, the pharmaceutical composition formulated into a unit dosage form contains 12 mg of Compound I or the pharmaceutically acceptable salt thereof. In some specific embodiments, the pharmaceutical composition formulated into a unit dosage form contains 14 mg of Compound I or the pharmaceutically acceptable salt thereof. In some specific embodiments, the pharmaceutical composition formulated into a unit dosage form contains 16 mg of Compound I or the pharmaceutically acceptable salt thereof. For example, for tablets or capsules, "a pharmaceutical composition formulated into a unit dosage form" means every one tablet or every one capsule.

The interval dosage regimen includes dosing periods and rest periods, and the pharmaceutical composition above mentioned may be administered one or more times a day during the dosing period. For example, administration of the pharmaceutical composition is performed daily during the dosing period, and then stopped for a period of time during the rest period, followed by the dosing period, and then the rest period, which can be repeated multiple times. The ratio of the dosing period to the rest period by the day is 2:0.5-5, preferably 2:0.5-3, more preferably 2:0.5-2, most preferably 2:0.5-1.

In some embodiments, the administration is continuously performed for 2 weeks and stopped for 2 weeks. In some embodiments, the administration is continuously performed once a day for 14 days, and then stopped for 14 days; followed by administration once a day for 14 days and then rest for 14 days; such interval dosage regimen with two-week dosing period and two-week rest period can be repeated several times.

In some embodiments, the administration is continuously performed for 2 weeks and stopped for 1 week. In some embodiments, the administration continuously performed once a day for 14 days, and then stopped for 7 days; followed by administration once a day for 14 days and then rest for 7 days; such interval dosage regimen with two-week dosing period and one-week rest period can be repeated several times.

In some embodiments, the administration is continuously performed for 5 days and stopped for 2 days. In some embodiments, the administration is performed once a day for 5 days, and then stopped for 2 days; followed by administration once a day for 5 days and then rest for 2 days; such interval dosage regimen with five-day dosing period and two-day rest period can be repeated several times.

Compound I can be administered in free base form or in the form of salts, hydrates and prodrugs thereof, wherein the prodrug is converted to the free base form of Compound I in vivo. For example, a pharmaceutically acceptable salt of Compound I is within the scope of this application, which can be produced from different organic and inorganic acids by methods well known in the art.

Unless otherwise indicated, the dosage or dose or amount and range provided herein are calculated based on the molecular weight of the free base of Compound I.

Unless otherwise indicated, q.d. means that administration once a day herein.

As used herein, the crystalline form of hydrochlorides of Compound I includes, but not limited to, the crystalline form A, B and C disclosed in Chinese Patent Application No. CN102344438A, wherein crystalline form A and B are substantially free of crystal water and other solvents, and crystalline form C is the one containing two molecules of crystal water. In some embodiments, the crystalline form of dihydrochloride of Compound I is crystalline form A.

Unless otherwise indicated, for the purposes of this application, the following terms used in this specification and claims should have the following meaning.

"Patient" refers to a mammal, preferably a human. In some embodiments, the patient refers to who undergoes treatment failure with standard treatment or whose disease lacks standard treatment.

"Pharmaceutically acceptable" refers to useful in preparation of the pharmaceutical composition which is generally safe, non-toxic and neither biologically nor otherwise undesirable, and acceptable for the use in human drugs.

"Pharmaceutically acceptable salts" include, but not limited to, acid addition salts formed with inorganic acids such as hydrochloric acid, hydrobromic acid, sulfuric acid, nitric acid, phosphoric acid, and the like; or formed with organic acids such as acetic acid, trifluoroacetic acid, propionic acid, caproic acid, heptanoic acid, cyclopentylpropionic acid, glycolic acid, pyruvic acid, lactic acid, malonic acid, succinic acid, malic acid, maleic acid, fumaric acid, tartaric acid, citric acid, benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, p-toluenesulfonic acid, 3-phenylpropionic acid, trimethylacetic acid, t-butylacetic acid, dodecyl sulfuric acid, gluconic acid, glutamic acid, hydroxy naphthoic acid, salicylic acid, stearic acid and the like.

"Therapeutically effective amount" means the amount of a compound, when administered to a human being for treating a disease, is sufficient to achieve therapeutic effect.

"Treatment/treating" means any administration of a therapeutically effective amount of a compound and includes:
(1) Inhibiting the disease in a human that is experiencing or exhibiting the pathology or symptoms of the disease (i.e., preventing the further development of pathology and/or symptoms), or (2) Ameliorating the disease in a human that is experiencing or exhibiting the pathology or symptoms of the disease (i.e., reversing the pathology and/or symptoms).

"PR" refers to partial relief, which means the sum of diameter of target tumor lesions decreases by more than 30% from baseline.

"PD" refers to progressive disease, which means the sum of diameter of target tumor lesions increases by more than 20% from baseline.

"SD" refers to stable disease, which means the change of the sum of diameter of target tumor lesions is between PR and PD, neither decreasing to PR nor increasing to PD.

"Treatment failure/failure of treatment" includes intolerance of toxic and side effects, progression of disease during treatment or recurrence after treatment; wherein intolerance includes the occurrence of grade IV hematological toxicity (grade III and above thrombocytopenia), grade III or above non-hematologic toxicity.

"Advanced" includes locally advanced.

EXAMPLES

Example 1 1-[[[4-(4-fluoro-2-methyl-1H-indol-5-yl)oxy-6-methoxyquinolin-7-yl]oxy]methyl]cyclopropylamine dihydrochloride (dihydrochloride of Compound I)

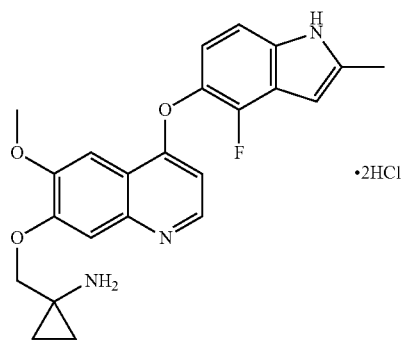 [SMILES: COc1cc2c(Oc3ccc4[nH]c(C)cc4c3F)ccnc2cc1OCC1(N)CC1]

1-[[[4-(4-fluoro-2-methyl-1H-indol-5-yl)oxy-6-methoxyquinolin-7-yl]oxy]methyl]-cyclopropylamine was prepared by the method of Example 24 in WO2008112407, and then the title compound was prepared referring to the preparation method in "Examples of salt formation" of the description of WO2008112407. Alternatively, it can be prepared by the method disclosed in Chinese Patent Application No. CN102344438A.

Example 2 Capsules containing 1-[[[4-(4-fluoro-2-methyl-1H-indol-5-yl)oxy-6-methoxyquinolin-7-yl]oxy]methyl]cyclopropylamine dihydrochloride (dihydrochloride of Compound I)

| Ingredients | amount (1000 capsules) |
|---|---|
| dihydrochloride of Compound I | 14.16 g (equivalent to 12 g of compound I) |
| Mannitol | 89 g |
| Microcrystalline cellulose | 138.4 g |
| Hydroxypropyl cellulose | 5.9 g |
| Magnesium stearate | 0.99 g |

The dihydrochloride of the Compound I was pulverized and sifted with a 80 mesh sieve, and then mixed with mannitol and hydroxypropyl cellulose uniformly, the prescribed amount of microcrystalline cellulose was added subsequently, mixed evenly and sifted with a 0.8 mm sieve; finally the prescribed amount of magnesium stearate was added and mixed evenly, the obtained mixture was filled into capsules. Capsules containing different amount of dihydrochloride of Compound I can be prepared referring to the same proportion and recipe mentioned above.

Example 3 The Efficacy on Gastric Cancer

1) Medical History

A sixty-year-old man experienced choking while eating for two years which aggravated for one month, was diagnosed with gastroesophageal junction cancer by gastroscopy on Nov. 28, 2013. On Dec. 11, 2013, he underwent radical operation under general anesthesia (partial resection of esophagus and stomach, gastroesophageal bow lower side anastomosis, and lymph nodes dissection), postoperative pathology showed moderately-poorly differentiated ulcerative gastroesophageal junction adenocarcinoma.

Postoperatively, the patient was treated with chemotherapy (Nedaplatin 160 mg+docetaxel 120 mg) for 4 cycles from Jan. 15 to May 18, 2014 in the thoracic surgery department; during chemotherapy, chest CT scan suggested that no abnormalities except for changes resulting from postoperation of gastroesophageal junction cancer. On Oct. 29, 2014, a chest CT scan showed increased and enlarged bilateral lungs nodules shadows, which was suspicious for liver multiple lesions, metastases and progressive disease. Afterwards, chemotherapy for 6 cycles was given on Oct. 30, Nov. 23, Dec. 18, 2014, Jan. 15, Feb. 9, Mar. 10, 2015, and the chemotherapy medication was Oxaliplatin (250 mg) and TIJIAO (tegafur, gimeracil and oteracil, oral anticancer agent of fluoropyrimidine derivative, capsule, 60 mg). On Jun. 8, 2015, CT scan showed that: 1. the anastomosis slightly thickened, and some bilateral lungs nodules enlarged than before; 2. the metastatic tumor in right lobe of liver enlarged and increased, suggesting that disease progressed. 60 mg of TIJIAO capsules were orally given continuously, CT scan on July 19$^{th}$ indicated that: 1. some bilateral lungs nodules enlarged, the metastatic tumor in right lobe of liver slightly enlarged. Comprehensive assessment suggested that disease progressed.

On Sep. 9, 2015, the capsules of dihydrochloride of Compound I were administered orally q.d. at a dose of 12 mg for treatment, and the administration was continuously performed for 2 weeks and rest for 1 week.

2) CT Scan Results

After 2 cycles of treatment with Compound I dihydrochloride capsules (12 mg, q.d.), enhanced CT scan showed that: the metastatic tumor in right lobe of liver enlarged than before, and the retroperitoneal lymph nodes enlarged, others were roughly the same as before. Efficacy was evaluated as SD (target lesion: upper posterior segment of the right lobe of liver 36 mm, left lobe of liver 16 mm; non-target lesions: multiple nodules in bilateral lungs, nodules shadows in the right lower pulmonary lobe)

3) Tolerance

After administration for 2 cycles, the patient was still under treatment without other obvious side effects.

Example 4 The Efficacy on Gastric Cancer

1) Medical History

A 47-year-old man underwent gastroscopy and gastric antrum masses biopsy on Jul. 3, 2014 due to abdominal pain and left neck masses. Pathological results indicated ulcerative moderately differentiated adenocarcinoma. A puncture biopsy of the left neck masses was performed, and the pathological result showed lymph nodes metastatic cancer.

Firstly, after 3 cycles of chemotherapy (TIJIAO and oxaliplatin), the efficacy was evaluated as PR; after 6 cycles of chemotherapy, plain and enhanced CT scan of thoracoabdominal and pelvic showed that: 1. Gastric antrum cancer, perigastric and abdominal paraaortic lymph nodes metastasis, in situ lesions and seemingly improved lymph nodes metastases; 2. no abnormality in the pelvis, the efficacy was evaluated as PD. Chemotherapy of paclitaxel and capecitabine was subsequently performed, and the efficacy was evaluated as PD.

On Sep. 17, 2015, the capsules of dihydrochloride of Compound I were administered orally q.d. at a dose of 12 mg for treatment, and the administration was continuously performed for 2 weeks and rest for 1 week. Clinical diagnosis before the treatment was: 1. gastric antrum cancer, 2. systemic multiple metastatic cancer (lymph nodes and lungs mostly). Clinical stage: stage IV, TNM stage: cT4N2M1.

2) CT Scan Results

| Cycle | CT Target lesions | Total of Target lesion | non-target lesions | Objective assessment of overall response |
|---|---|---|---|---|
| Before administration | Left supraclavicular enlarged lymph node 23.5 mm, Abdominal lymph node① 16 mm, Abdominal lymph node② 21.4 mm, perigastric lymph node 16.6 mm. | 77.5 mm | Lung, Kidney | |
| Second cycle | Left supraclavicular enlarged lymph node 16.6 mm, Abdominal lymph node① 9 mm, Abdominal lymph node② 14.7 mm, perigastric lymph node 17 mm. | 57.3 mm | Lung, Kidney | SD |
| Fourth cycle | Left supraclavicular enlarged lymph node 16.3 mm, Abdominal lymph node① 6.9 mm, | 53 mm | Lung, Kidney | PR |

| Cycle | CT Target lesions | Total of Target lesion | non-target lesions | Objective assessment of overall response |
|---|---|---|---|---|
| | Abdominal lymph node② 16.6 mm, perigastric lymph node 13.2 mm. | | | |

3) Tolerance

After administration for 4 cycles, side effects were basically tolerable, facial skin pigmentation was lightened, and mental state was better than before, the patient was still under treatment of capsules of dihydrochloride of Compound I.

Example 5 The Efficacy on Gastric Cancer

1) Medical History

A 45-year-old woman detected left breast lump, puncture biopsy was performed in December 2014, and pathology showed suspicious lesion and chronic mastitis in Left breast. On May 15, 2015, pathological examination of left supraclavicular lymph node showed a few fibers and inflammatory cells. On Jun. 12, 2015, invasive tumor was observed by gastroscope, and pathology showed signet ring cell carcinoma. On Jun. 18, 2015, core needle biopsy of left breast was performed, and pathology showed invasive carcinoma and gastric cancer with breast metastasis. Three cycles of chemotherapy treatment of Xeloda (capecitabine, 1500 mg) and oxaliplatin (209.3 mg) were performed from Jun. 25, 2015, efficacy was evaluated as PD.

Then the capsules of dihydrochloride of Compound I were administered orally q.d. at 12 mg for treatment, and the administration was continuously performed for 2 weeks and rest for 1 week.

2) CT Scan Results

After 2 cycles of treatment, efficacy was evaluated as SD by CT scan.

3) Tolerance

After 2 cycles of administration, the side effects were basically tolerable except for occasional heart palpitations and discomfort, the patient was still under treatment of capsules of dihydrochloride of Compound I.

Example 6 The Efficacy on Gastric Cancer

1) Medical History

A 60-year-old man, experienced emaciation and hypodynamia for 3 months, was diagnosed with gastric adenocarcinoma by gastroscopy in June 2015, then radical surgery for gastric cancer was performed, and postoperative pathology showed moderately differentiated and polypoid gastric tubular adenocarcinoma. In July 2015, CT scan revealed liver metastasis. From July to August 2015, XELOX regimen (oxaliplatin+capecitabine) was performed for 2 cycles, and the CT scan showed enlarged liver lesions. In September 2015, the chemotherapy regimen of Paclitaxel and TIJIAO was performed for 5 cycles instead, then reexamined and evaluated as PD. In December 2015, the capsules of dihydrochloride of Compound I were administered orally q.d. at a dose of 12 mg, the administration was continuously performed for 2 weeks and rest for 1 week. Clinical diagnosis before the treatment was: 1. gastric cancer with liver metastasis; clinical stage: T3N3aM0; TNM stage: T3N3aM0.

2) CT Scan Results

| cycle | CT target lesions | total of Target lesion | non-target lesions | objective assessment of overall response |
|---|---|---|---|---|
| Before administration | Liver 41 mm, Liver 22 mm. | 63 mm | Stomach wall | |
| Second cycle | Liver 41 mm, Liver 19 mm. | 60 mm | Stomach wall | SD |
| Fourth cycle | Liver 40 mm, Liver 19 mm. | 59 mm | Stomach wall | SD |
| Sixth cycle | Liver 41 mm, Liver 16 mm. | 57 mm | Stomach wall, perihepatic ascites (small amount) | SD |
| Eighth cycle | Liver 42 mm, Liver 16 mm. | 58 mm | Stomach wall, perihepatic ascites (small amount) | SD |
| Tenth cycle | Liver 41 mm, Liver 18 mm. | 59 mm | Stomach wall, abdomen, pelvic effusion | SD |
| Twelfth cycle | Liver 41 mm, Liver 18 mm. | 59 mm | Stomach wall, abdomen, pelvic effusion | SD |

Note:
Two CT target lesions in the above table were selected from lesions in the liver. For example, "Liver 41 mm, Liver 22 mm" refers to two lesions in the liver, one lesion length was 41 mm and the other was 22 mm.

Example 7 The Efficacy on Gastric Cancer

1) Medical History

A 52-year-old man experienced choking after eating without obvious inducement, in March 2014, gastroscopy revealed gastric cancer, and pathology showed gastric body and gastric sinus adenocarcinoma. In January 2015, radical total gastrectomy and esophago-jejunum Roux-en-Y anastomosis were performed under general anesthesia. Postoperative pathology displayed that: total gastrectomy specimen, gastric body and lesser curvature adenocarcinoma, part of which was mucinous adenocarcinoma, grade II-III, ulcer-like lump which was 6*4.5*1.5 cm, the tumor infiltrated total layers of stomach wall to adipose connective tissue which was outside of the serosa, no residual carcinoma in the upper and lower incisal margins, metastasis was observed in the lymph nodes of the lesser curvature and greater curvature of stomach. Lauren classification: mixed type.

From June to July 2014, the chemotherapy regimen (paclitaxel liposome for injection and 5-fluorouracil) was performed for 1 cycle, efficacy was not evaluated. From July to October 2014, the chemotherapy regimen (paclitaxel liposomes for injection+oxaliplatin+5-fluorouracil) was performed for 4 cycles, followed by CT scan, which suggested PD. From March to April 2015, the chemotherapy regimen (Oxaliplatin+Capecitabine) was performed for 2 cycles. In September 2015, chest and abdomen CT scan showed progression after second-line treatment for gastric cancer.

On Sep. 12, 2015, the capsules of dihydrochloride of Compound I were administered orally q.d. at a dose of 12 mg, the administration was continuously performed for 2 weeks and rest for 1 week. Clinical diagnosis before treatment: gastric cancer. Clinical stage: stage IV, TNM stage: T4aN1M1.

2) CT Scan Results

| Cycle | Target lesions | Total of Target lesion | non-target lesions | Objective assessment of overall response |
|---|---|---|---|---|
| Before administration | Anterior pancreatic neck lymph node 22.1 mm, posterior Pancreatic neck lymph node 23.9 mm, Hepatic caudate lobe nodule 10.6 mm | 56.6 mm | Lung | |
| Second cycle | Anterior pancreatic neck lymph node 22.0 mm, posterior pancreatic neck lymph node 26.1 mm, Hepatic caudate lobe nodule 17.4 mm. | 65.5 mm | Lung | SD |

What is claimed is:

1. A method for treating gastric cancer, comprising orally administering to a patient in need of treatment a daily dosage of 12 mg of Compound I or a pharmaceutically acceptable salt thereof for 2 weeks and rest for 1 week, wherein Compound I has the following structure,

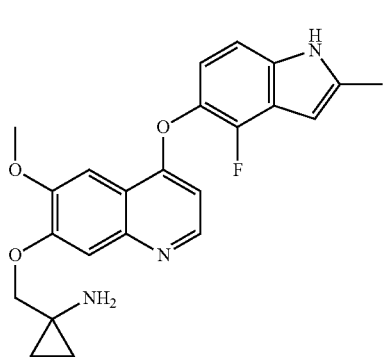

I wherein previous treatment of the patient with one or more taxane antineoplastic agents, camptothecin antineoplastic agents, adriamycin antineoplastic agents, platinum complexes, and/or fluoropyrimidine derivatives has failed.

2. The method according to claim 1, wherein the gastric cancer is advanced and/or metastatic gastric cancer.

3. The method according to claim 1, wherein the gastric cancer is moderately differentiated or poorly differentiated gastric cancer.

4. The method according to claim 1, wherein the gastric cancer is gastric adenocarcinoma or gastroesophageal junction adenocarcinoma.

5. The method according to claim 4, wherein the gastric adenocarcinoma is papillary adenocarcinoma, tubular adenocarcinoma, mucinous adenocarcinoma, signet ring cell carcinoma, or a mixed-type adenocarcinoma of the above histological types.

6. The method according to claim 1, wherein the pharmaceutically acceptable salt thereof is a dihydrochloride of Compound I.

7. The method according to claim 1, wherein Compound I or the pharmaceutically acceptable salt thereof is administered orally once daily.

8. A method of treating gastric cancer comprising orally administering to a patient in need thereof a pharmaceutical composition comprising Compound I or a pharmaceutically acceptable salt thereof, and at least one pharmaceutically acceptable carrier at a daily dosage of 12 mg of Compound I or the pharmaceutically acceptable salt thereof for 2 weeks and rest for 1 week, wherein Compound I has the following structure,

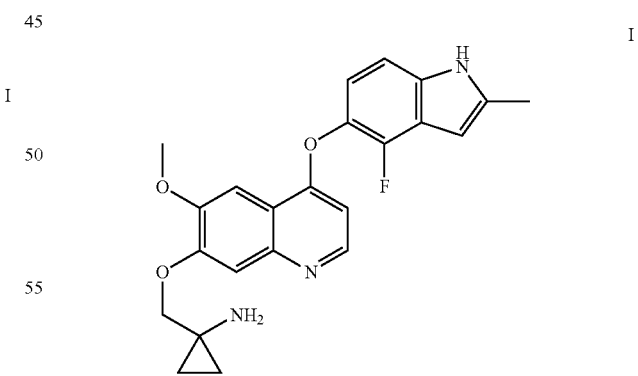

I wherein previous treatment of the patient with one or more taxane antineoplastic agents, camptothecin antineoplastic agents, adriamycin antineoplastic agents, platinum complexes and/or fluoropyrimidine derivatives has failed.

9. The method according to claim 8, wherein the gastric cancer is one or more of gastroesophageal junction adenocarcinoma, papillary adenocarcinoma, tubular adenocarcinoma, mucinous adenocarcinoma, and signet ring cell carcinoma.

10. The method of claim 8, wherein the pharmaceutically acceptable salt thereof is a dihydrochloride of Compound I.

11. The method of claim 8, wherein the pharmaceutical composition is provided as a unit dosage form.

12. The method of claim 8, wherein the pharmaceutical composition is administered orally once daily.

13. The method of claim 8, wherein the pharmaceutical composition is provided as tablets or capsules.

* * * * *